(12) United States Patent
Fraser et al.

(10) Patent No.: US 11,291,783 B2
(45) Date of Patent: Apr. 5, 2022

(54) ELECTRONIC VAPOR PROVISION DEVICE WITH ABSORBENT ELEMENT

(71) Applicant: NICOVENTURES HOLDINGS LIMITED, London (GB)

(72) Inventors: Rory Fraser, London (GB); Howard Rothwell, London (GB); Marina Trani, London (GB); Carolyn Garnett, London (GB)

(73) Assignee: NICOVENTURES TRADING LIMITED, London (GB)

( * ) Notice: Subject to any disclaimer, the term of this patent is extended or adjusted under 35 U.S.C. 154(b) by 306 days.

(21) Appl. No.: 16/327,085

(22) PCT Filed: Aug. 9, 2017

(86) PCT No.: PCT/GB2017/052340
§ 371 (c)(1),
(2) Date: Feb. 21, 2019

(87) PCT Pub. No.: WO2018/037206
PCT Pub. Date: Mar. 1, 2018

(65) Prior Publication Data
US 2019/0208821 A1    Jul. 11, 2019

(30) Foreign Application Priority Data

Aug. 25, 2016  (GB) .................... 1614477

(51) Int. Cl.
*A24F 47/00* (2020.01)
*H05B 1/02* (2006.01)
(Continued)

(52) U.S. Cl.
CPC ............. *A61M 15/06* (2013.01); *A24F 40/40* (2020.01); *A61M 11/042* (2014.02);
(Continued)

(58) Field of Classification Search
None
See application file for complete search history.

(56) References Cited

U.S. PATENT DOCUMENTS

| | | | |
|---|---|---|---|
| 2011/0120455 | A1 | 5/2011 | Murphy |
| 2011/0226236 | A1 | 9/2011 | Buchberger |
| | | (Continued) | |

FOREIGN PATENT DOCUMENTS

| | | |
|---|---|---|
| AU | 2017315219 B2 | 10/2019 |
| CN | 101869356 A | 10/2010 |
| | (Continued) | |

OTHER PUBLICATIONS

Communication pursuant to Article 94(3) EPC for Application No. 17752453.5, dated Mar. 16, 2021, 17 pages.
(Continued)

*Primary Examiner* — Dennis R Cordray
(74) *Attorney, Agent, or Firm* — Patterson Thuente Pedersen, P.A.

(57) ABSTRACT

A component of an electronic vapor provision device with a reservoir for storing source liquid, an atomizer for vaporizing source liquid from the reservoir and delivering vapor into an air flow path through the device, and an electrical power supply for providing electrical power to the atomizer comprises an absorbent element to collect source liquid escaped from the reservoir and located so as to be upstream of the atomizer with respect to an air flow direction along the air flow path when the component is assembled into the electronic vapor provision device.

18 Claims, 3 Drawing Sheets

(51) Int. Cl.
*H05B 3/46* (2006.01)
*A61M 15/06* (2006.01)
*A61M 11/04* (2006.01)
*A24F 40/40* (2020.01)
*A61M 16/00* (2006.01)
*A24F 40/10* (2020.01)
*A24B 15/167* (2020.01)

(52) U.S. Cl.
CPC .............. *H05B 1/0297* (2013.01); *H05B 3/46* (2013.01); *A24B 15/167* (2016.11); *A24F 40/10* (2020.01); *A61M 2016/0021* (2013.01); *A61M 2205/3331* (2013.01); *A61M 2205/3653* (2013.01); *A61M 2205/7527* (2013.01); *A61M 2205/8206* (2013.01)

(56) References Cited

U.S. PATENT DOCUMENTS

| | | |
|---|---|---|
| 2013/0255675 A1 | 10/2013 | Liu |
| 2013/0306065 A1 | 11/2013 | Thorens et al. |
| 2013/0319438 A1 | 12/2013 | Liu |
| 2014/0060524 A1 | 3/2014 | Liu |
| 2014/0261399 A1 | 9/2014 | Murphy |
| 2015/0201674 A1 | 7/2015 | Dooly et al. |
| 2015/0245667 A1 | 9/2015 | Memari |
| 2015/0272216 A1 | 10/2015 | Dai et al. |
| 2015/0342256 A1 | 12/2015 | Chen |
| 2015/0366267 A1 | 12/2015 | Liu |
| 2016/0000147 A1 | 1/2016 | Li |
| 2016/0073692 A1 | 3/2016 | Alarcon et al. |
| 2016/0143364 A1 | 5/2016 | DePiano et al. |
| 2016/0143365 A1 | 5/2016 | Liu |
| 2016/0192710 A1 | 7/2016 | Liu |
| 2020/0000151 A1 | 1/2020 | Fraser et al. |

FOREIGN PATENT DOCUMENTS

| | | |
|---|---|---|
| CN | 102014996 A | 4/2011 |
| CN | 102264249 A | 11/2011 |
| CN | 102264420 A | 11/2011 |
| CN | 103099319 A | 5/2013 |
| CN | 203137029 U | 8/2013 |
| CN | 103418062 A | 12/2013 |
| CN | 103948174 | 7/2014 |
| CN | 203762301 U | 8/2014 |
| CN | 203851809 U | 10/2014 |
| CN | 203873010 U | 10/2014 |
| CN | 204232300 U | 4/2015 |
| CN | 104605482 A | 5/2015 |
| CN | 205456063 U | 8/2016 |
| EP | 2979555 A1 | 2/2016 |
| JP | 2012506263 A | 3/2012 |
| JP | 2015506182 A | 3/2015 |
| JP | 6831047 B2 | 2/2021 |
| KR | 20120105655 A | 9/2012 |
| KR | 20130031550 A | 3/2013 |
| RU | 2489948 C2 | 8/2013 |
| RU | 2527351 C2 | 8/2014 |
| RU | 2620751 C2 | 5/2017 |
| RU | 2734867 C2 | 10/2020 |
| WO | WO-0102040 A1 | 1/2001 |
| WO | WO-2013116572 A1 | 8/2013 |
| WO | WO-2013159245 A1 | 10/2013 |
| WO | WO-2014012906 | 1/2014 |
| WO | WO-2014177859 | 11/2014 |
| WO | WO-2015077645 | 5/2015 |
| WO | WO-2015108816 A2 | 7/2015 |
| WO | WO-2016054580 A1 | 4/2016 |
| WO | WO-2016123764 | 8/2016 |
| WO | WO-2016156609 A1 | 10/2016 |
| WO | WO-2017028295 | 2/2017 |

OTHER PUBLICATIONS

International Preliminary Report on Patentability for Application No. PCT/GB2017/052340, dated Mar. 7, 2019, 10 pages.
International Search Report and Written Opinion for Application No. PCT/GB2017/052340, dated Nov. 8, 2017, 15 pages.
Office Action for Chinese Application No. 201780051670.8, dated Nov. 3, 2020, 20 pages.
Search report dated Apr. 30, 2021 for Russian Application No. 2020134006, 2 pages.
Search Report under Section 17(5) for GB Application No. 1614477.6 dated Feb. 15, 2018, 3 pages.

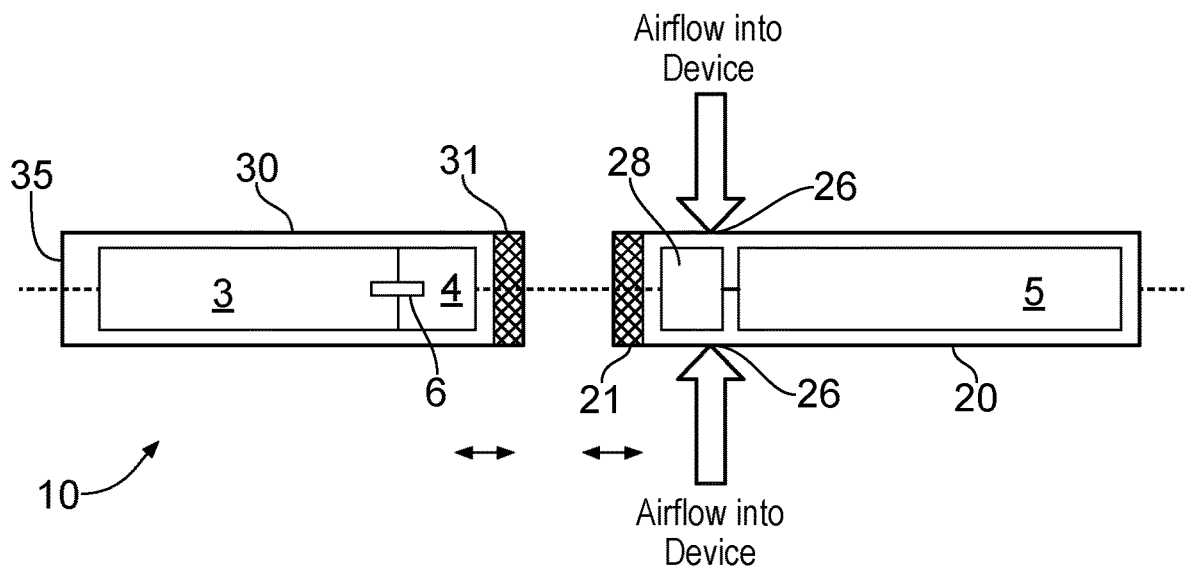
FIG. 1
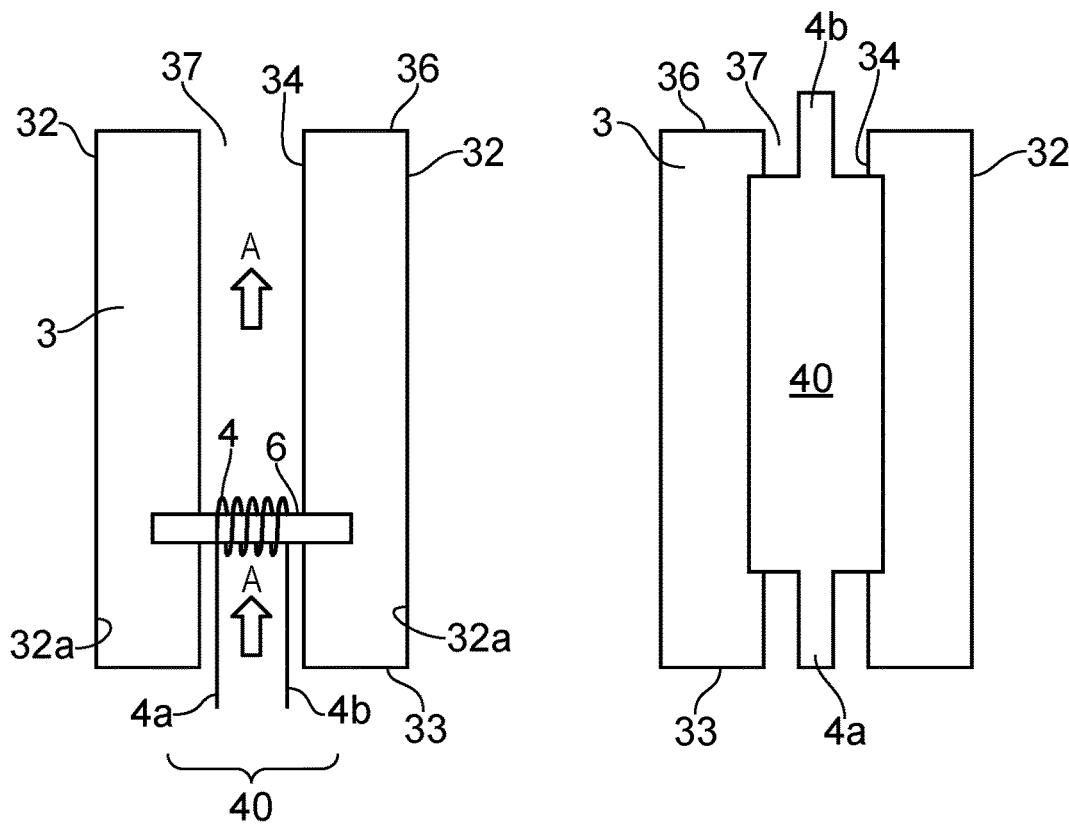
FIG. 2
FIG. 3

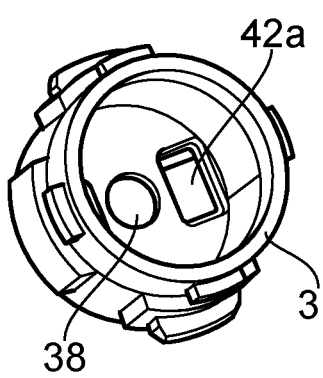
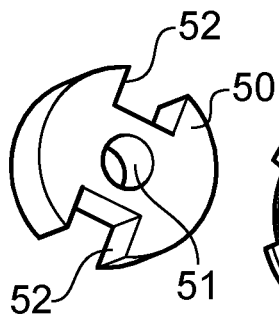
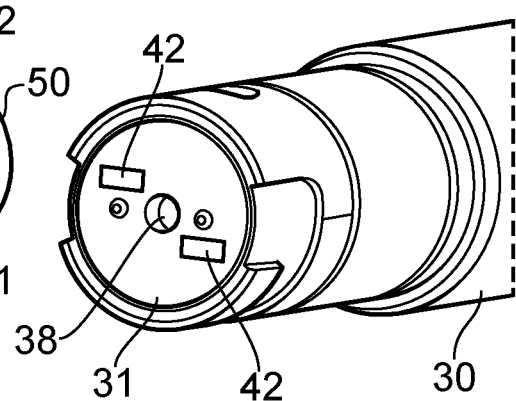
FIG. 7A    FIG. 7B    FIG. 7C
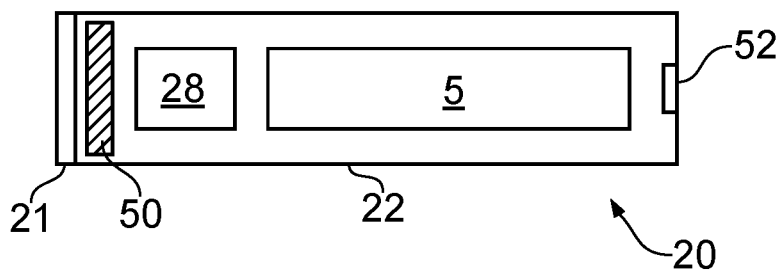
FIG. 8
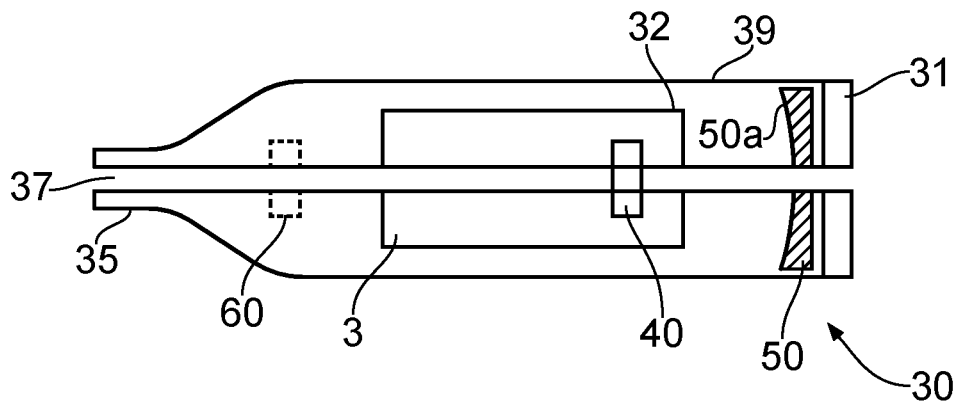
FIG. 9

ELECTRONIC VAPOR PROVISION DEVICE WITH ABSORBENT ELEMENT

PRIORITY CLAIM

The present application is a National Phase entry of PCT Application No. PCT/GB2017/052340, filed Aug. 9, 2017, which claims priority from GB Patent Application No. 1614477.6, filed Aug. 25, 2016, which is hereby fully incorporated herein by reference.

TECHNICAL FIELD

The present disclosure relates to electronic vapor provision devices and components of electronic vapor provision devices.

BACKGROUND

Aerosol or vapor provision systems such as e-cigarettes generally contain a reservoir of a source liquid containing a formulation, typically including nicotine, from which an aerosol is generated, such as through vaporization or other means. Thus an aerosol source for a vapor provision system may comprise a heating element coupled to a portion of the source liquid from the reservoir. In some systems, the heating element and reservoir are comprised within a first section or component which is connectable to a second section or component housing a battery to provide electrical power to the heating element. This first section may be referred to as a cartomizer, and can be disposable to be replaced when the source liquid has been consumed. In use, a user inhales on the device to activate the heating element which vaporizes a small amount of the source liquid, which is thus converted to an aerosol for inhalation by the user.

The reservoir may hold free-flowing source liquid or may house some absorbent material which is soaked in source liquid. The reservoir is designed so that the source liquid can exit the reservoir, reach the heating element and be vaporized when the heating element is at a high temperature; this may be by use of a porous wicking element which reaches into the reservoir and is physically coupled to the heating element. However, aside from this intended result for the source liquid, construction of the reservoir and atomizer may allow source liquid to escape from the reservoir without being vaporized, such as by slow seepage, or by changes in ambient pressure or temperature or a momentary pressure wave produced by physical impact forcing liquid through small apertures. Points vulnerable to leakage include joins between separate sections of the reservoir wall, joints where the reservoir is connected to adjacent components, and around a removable cap or plug for filling the reservoir and where the wicking element penetrates the reservoir wall. Liquid escaping from the reservoir at such places may not be successfully vaporized at the heating element and is liable to travel to undesirable locations, such as reaching the battery or control electronics where it may cause short circuiting or corrosion damage, or leaking out from the electronic cigarette or a component thereof altogether and soiling the user or his belongings.

Approaches aimed at mitigating these problems are of interest.

SUMMARY

According to a first aspect of certain embodiments described herein, there is provided a component of an electronic vapor provision device, the device having a reservoir for storing source liquid, an atomizer for vaporizing source liquid from the reservoir and delivering vapor into an air flow path through the device, and an electrical power supply for providing electrical power to the atomizer, in which the component comprises an absorbent element to collect source liquid escaped from the reservoir, the absorbent element located so as to be upstream of the atomizer with respect to an air flow direction along the air flow path when the component is assembled into the electronic vapor provision device. The absorbent element may be located so as to be between the atomizer and the electrical power supply in the assembled electronic vapor provision device along a liquid flow path from the atomizer to the electrical power supply.

The absorbent element may inhibit said escaped liquid from leaving the component. Alternatively or additionally the absorbent element may inhibit said escaped liquid from reaching the electrical power supply. The electrical power supply may comprise a battery. Alternatively or additionally, the electrical power supply may comprise control circuitry for controlling the provision of electrical power to the atomizer.

The absorbent element may be located adjacent to an end face of the component. The end face of the component may be at an end of the component connectable to another component of the electronic vapor provision device.

The component may be a cartomizer component housing the reservoir and the atomizer and being connectable to a power component housing the electrical power supply, and the absorbent element is located so as to inhibit said escaped liquid from leaving the cartomizer component, and also from reaching the electrical power supply when the cartomizer component is connected to the power component. The absorbent element may be mounted within an end cap of the cartomizer component which is configured to allow electrical contact with an electrical power supply housed in a power component of the electronic vapor provision device to which the said component is connectable.

Alternatively, the component may be a power component housing the electrical power supply and connectable to a cartomizer component housing the reservoir and the atomizer, and the absorbent element is located so as to inhibit said escaped liquid from reaching the electrical power supply when the power component is connected to the cartomizer component.

The absorbent element may have a planar shape and a thickness orthogonal to its plane in the range of 1 mm to 10 mm.

The absorbent element may be formed from an absorbent material comprising polypropylene and polyethylene. For example, the absorbent material may comprise 50% polypropylene and 50% polyethylene, or polypropylene in the range of 45% to 55% and polyethylene in the range of 55% to 45%, or polypropylene in the range of 48% to 52% and polyethylene in the range of 52% to 48%, or polypropylene in the range of 49% to 51% and polyethylene in the range of 51% to 48%.

The absorbent element may be formed from an absorbent material which increases its volume by not more than 1%, 3%, 5%, 10% or 20% when fully saturated.

According to a second aspect of certain embodiments, there is provided an electronic vapor provision device comprising a component according to the first aspect.

The component may be separably connectable to another component of the electronic vapor provision device, or the component may be a permanent component of the electronic vapor provision device.

These and further aspects of certain embodiments are set out in the appended independent and dependent claims. It will be appreciated that features of the dependent claims may be combined with each other and features of the independent claims in combinations other than those explicitly set out in the claims. Furthermore, the approach described herein is not restricted to specific embodiments such as set out below, but includes and contemplates any appropriate combinations of features presented herein. For example, an electronic vapor provision device or a component for an electronic vapor provision device may be provided in accordance with approaches described herein which includes any one or more of the various features described below as appropriate.

BRIEF DESCRIPTION OF THE DRAWINGS

Various embodiments will now be described in detail by way of example only with reference to the accompanying drawings in which:

FIG. 1 shows a simplified schematic cross-sectional view of an example electronic cigarette or vapor provision device.

FIG. 2 shows a schematic cross-sectional view of a first example aerosol source of an electronic cigarette, comprising a reservoir and an atomizer.

FIG. 3 shows a schematic cross-sectional view of a second example aerosol source of an electronic cigarette, comprising a reservoir and an atomizer.

FIG. 7A shows a perspective interior view of a further example end cap for a cartomizer.

FIG. 7B shows a perspective view of an example absorbent element for use with the end cap of FIG. 7A.

FIG. 7C shows a perspective end view of an example cartomizer with the end cap of FIG. 7A.

FIG. 8 shows a schematic cross-sectional view of an example power component of an electronic cigarette including an example absorbent element.

FIG. 9 shows a schematic cross-sectional view of a further example cartomizer component including a further example absorbent element.

DETAILED DESCRIPTION

Figure 4:
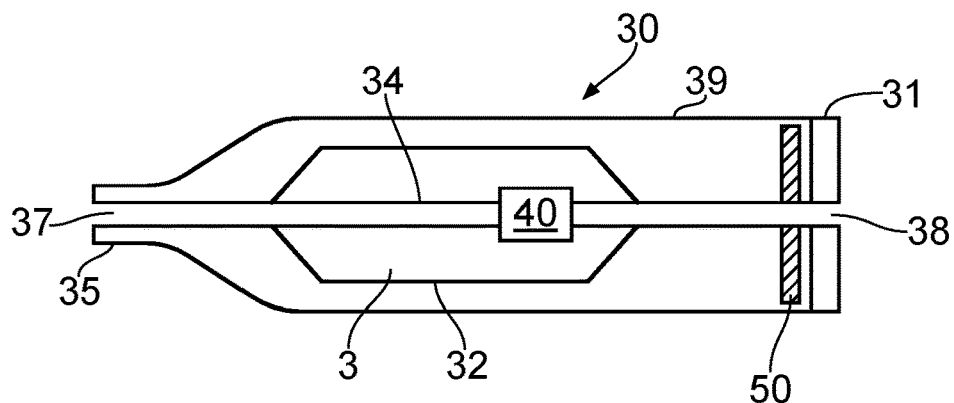
FIG. 4 shows a schematic cross-sectional view of an example cartomizer component of an electronic cigarette including an example absorbent element.

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to (but is not limited to) electronic aerosol or vapor provision systems, such as e-cigarettes. Throughout the following description the terms "e-cigarette" and "electronic cigarette" may sometimes be used; however, it will be appreciated these terms may be used interchangeably with aerosol (vapor) provision system or device. Similarly, "aerosol" may be used interchangeably with "vapor".

As used herein, the term "component" is used to refer to a part, section, unit, module, assembly or similar of an electronic cigarette that incorporates several smaller parts or elements, often within an exterior housing or wall. An electronic cigarette may be formed or built from one or more such components, and the components may be removably connectable to one another, or may be permanently joined together during manufacture to define the whole electronic cigarette.

FIG. 1 is a highly schematic diagram (not to scale) of an example aerosol/vapor provision system such as an e-cigarette 10. The e-cigarette 10 has a generally cylindrical shape, extending along a longitudinal axis indicated by a dashed line, and comprises two main components, namely a control or power component or section 20 and a cartridge assembly or section 30 (sometimes referred to as a cartomizer, clearomizer or atomizer) that operates as a vapor generating component.

The cartridge assembly 30 includes a reservoir 3 containing a source liquid comprising a liquid formulation from which an aerosol is to be generated, for example containing nicotine. As an example, the source liquid may comprise around 1 to 3% nicotine and 50% glycerol, with the remainder comprising roughly equal measures of water and propylene glycol, and possibly also comprising other components, such as flavorings. The reservoir 3 has the form of a storage tank, being a container or receptacle in which source liquid can be stored such that the liquid is free to move and flow within the confines of the tank. Alternatively, the reservoir 3 may contain a quantity of absorbent material such as cotton wadding or glass fiber which holds the source liquid within a porous structure. The reservoir 3 may be sealed after filling during manufacture so as to be disposable after the source liquid is consumed, or may have an inlet port or other opening through which new source liquid can be added. The cartridge assembly 30 also comprises an electrical heating element or heater 4 located externally of the reservoir tank 3 for generating the aerosol by vaporization of the source liquid by heating. An arrangement such as a wick or other porous element 6 may be provided to deliver portions of source liquid from the reservoir 3 to the heater 4. The wick 6 has one or more parts located inside the reservoir 3 so as to be able to absorb source liquid and transfer it by wicking or capillary action to other parts of the wick 6 that are in contact with the heater 4. This liquid is thereby heated and vaporized, to be replaced by a new portion of liquid transferred to the heater 4 by the wick 3. The wick therefore extends through a wall that defines the interior volume of the reservoir tank 3, and might be thought of as a bridge or conduit between the reservoir 3 and the heater 4. A heater and wick (or similar) combination is sometimes referred to as an atomizer, and the reservoir with its source liquid plus the atomizer may be collectively referred to as an aerosol source. Various designs are known, in which the parts may be differently arranged compared to the highly schematic representation of FIG. 1. For example, the wick 6 may be an entirely separate element from the heater 4, or the heater 4 may be configured to be porous and able to perform the wicking function directly (a metallic mesh, for example). Regardless of the implementation, the parts will be configured to form a liquid flow path by which the source liquid is able to travel from the interior of the reservoir 3 to the vicinity and surface of the heater 4 for heating and vaporization. This is the intended fluid path, whereby liquid is delivered to the heater and should be successfully vaporized and thereby prevented from arriving at any unwanted location.

The cartridge assembly 30 also includes a mouthpiece 35 having an opening or air outlet through which a user may inhale the aerosol generated by the heater 4.

The power component 20 includes a cell or battery 5 (referred to herein after as a battery, and which may be re-chargeable) to provide power for electrical components of the e-cigarette 10, in particular the heater 4. Additionally, there is a printed circuit board 28 and/or other electronics or circuitry for generally controlling the e-cigarette. The control electronics/circuitry connect the heater 4 to the battery 5 when vapor is required, for example in response to a signal from an air pressure sensor or air flow sensor (not shown) that detects an inhalation on the system 10 during which air enters through one or more air inlets 26 in the wall of the power component 20. When the heating element 4 receives power from the battery 5, the heating element 4 vaporizes source liquid delivered from the reservoir 3 by the wick 6 to generate the aerosol, and this is then inhaled by a user through the opening in the mouthpiece 35. The aerosol is carried from the aerosol source to the mouthpiece 35 along an air channel (not shown) that connects the air inlet 26 to the aerosol source to the air outlet when a user inhales on the mouthpiece 35. An air flow path through the electronic cigarette is hence defined, between the air inlet(s) (which may or may not be in the power component) to the atomizer and on to the air outlet at the mouthpiece. In use, the air flow direction along this air flow path is from the air inlet to the air outlet, so that the atomizer can be described as lying downstream of the air inlet and upstream of the air outlet.

Herein, the term "electrical power supply" is used to refer to either or both of the battery and the control circuitry.

In this particular example, the power section 20 and the cartridge assembly 30 are separate parts detachable from one another by separation in a direction parallel to the longitudinal axis, as indicated by the solid arrows in FIG. 1. The components 20, 30 are joined together when the device 10 is in use by cooperating engagement elements 21, 31 (for example, a screw or bayonet fitting) which provide mechanical and electrical connectivity between the power section 20 and the cartridge assembly 30. This is merely an example arrangement, however, and the various components may be differently distributed between the power section 20 and the cartridge assembly section 30, and other components and elements may be included. The two sections may connect together end-to-end in a longitudinal configuration as in FIG. 1, or in a different configuration such as a parallel, side-by-side arrangement. The system may or may not be generally cylindrical and/or have a generally longitudinal shape. Either or both sections may be intended to be disposed of and replaced when exhausted (the reservoir is empty or the battery is flat, for example), or be intended for multiple uses enabled by actions such as refilling the reservoir and recharging the battery. Alternatively, the e-cigarette 10 may be a unitary device (disposable or refillable/re-chargeable) that cannot be separated into two parts, in which case all components are comprised within a single body or housing. Embodiments and examples of the present disclosure are applicable to any of these configurations and other configurations of which the skilled person will be aware.

The example device in FIG. 1 is presented in a highly schematic format. FIGS. 2 and 3 show more detailed representations of aerosol sources according to examples, indicating relative positions of the tank, heater and wick.

FIG. 2 shows a cross-sectional side view of an aerosol source. A reservoir tank 3 has an outer wall 32 and an inner wall 34, each of which is generally cylindrical. The inner wall 34 is centrally disposed within the outer wall 32 to define an annular space between the two walls; this is the interior volume of the tank 3 intended to hold source liquid. The tank is closed at its lower end (in the orientation depicted) by a bottom wall 33 and at its top end by an upper wall 36. The central space encompassed by the inner wall 34 is an airflow passage or channel 37 which at its lower end receives air drawn into the electronic cigarette (such as via air intakes 26 shown in FIG. 1), and at its upper end delivers aerosol for inhalation (such as through the mouthpiece 35 in FIG. 1).

Disposed within the airflow channel 37 is an atomizer 40 comprising a heater 4 and a wick 6. The wick 6, an elongate porous element that may, for example, be rod-shaped and formed from fibers, is arranged across the airflow passage (shown as closer to the lower end of the tank 3, but it may be positioned higher) so that its ends pass through apertures in the inner wall 34 and reach into the interior volume of the tank 3 to absorb source liquid therein. The apertures (not shown) may be sealed to minimize source liquid leakage from the tank 3 into the airflow channel 37; nevertheless leakage may still arise. The heater 4 is an electrically powered heating element in the form of a wire coil wrapped around the wick 6. Connecting leads 4a, 4b join the heater 4 to a circuit (not shown) for the provision of electrical power from a battery. The aerosol source will be disposed within the housing of a cartridge assembly section (cartomizer) of an electronic cigarette, with a mouthpiece arranged at its top end and a controller and battery arranged at its lower end (possibly in a separable component). Note that the outer wall 32 of the tank 3 may or may not also be a wall of the cartridge assembly housing. If these walls are shared, the cartridge assembly may be intended to be disposable when the source liquid has been consumed, to be replaced by a new cartridge assembly connectable to an existing battery/power section, or may be configured so that the reservoir tank 3 can be refilled with source liquid. If the tank wall and the housing wall are different, the tank 3 or the whole aerosol source may be replaceable within the housing when the source liquid is consumed, or may be removable from the housing for the purpose of refilling. These are merely example arrangements and are not intended to be limiting.

In use, when the aerosol source within its assembly housing is joined to a battery section (separably or permanently depending on the e-cigarette design), and a user inhales through the mouthpiece, air drawn into the device through an inlet or inlets enters the airflow channel 37. The heater 4 is activated to produce heat; this causes source liquid brought to the heater 4 by the wick 6 to be heated to vaporization. The vapor is carried by the flowing air further along the airflow channel 37 to the mouthpiece of the device to be inhaled by the user. The arrows A indicate the airflow and its direction along the air flow path through the device.

FIG. 3 shows a cross-sectional side view of an alternative example aerosol source. As in the FIG. 2 example, the tank 3 is an annular space formed between an outer wall 32 and an inner wall 34, with the interior space of the tubular inner wall 34 providing an airflow channel 37. In this example, however, the rod-shaped wick and coiled heating element are replaced by an atomizer 40 in which a single entity provides both the wicking and heating functions. An electrically conductive mesh can be used for this, for example, where the conductive characteristic allows the atomizer to receive electrical power and heat up, while the mesh structure allows a wicking action. The atomizer 40 is again arranged across the airflow channel 37 with parts passing through the inner wall 34 into the interior volume of the tank 3. However, in this example, the atomizer 40 has an elongate planar configuration and is arranged such that its long edges reach into the reservoir, and its short ends are at each end of the airflow passage 37. These ends 4a, 4b are connected to a battery by appropriate arrangement of electrical conductors (not shown). Thus, a larger area of vaporizing surface is offered to air flowing through the airflow channel. Apertures where the edges of the atomizer extend into the atomizer may or may not be sealed to minimize leakage into the air flow channel 37, but some leakage may occur nevertheless.

FIGS. 2 and 3 are merely examples of aerosol sources to illustrate various alternatives available for achieving aerosol generation. Other configurations can achieve the same effect, and the invention is not limited in this regard. In particular, the reservoir may have other formats and the coupling between the reservoir and the atomizer may differ. Whichever configuration is adopted, in any design which includes a reservoir in the form of a tank, container, receptacle or similar volume for holding the source liquid will be potentially vulnerable to unwanted leakage of the source liquid from the reservoir, where such leakage may be along paths, routes and directions that do not take the source liquid to a location where it can be vaporized. The construction of the reservoir may produce potential leakage points, such as where sections of the reservoir wall are joined together, or where the reservoir is joined to adjacent parts. Also, seals which may be included at potential weak spots such as where the wick passes through the reservoir wall or where an access cap or lid is provided for refilling the reservoir might be imperfect. Furthermore, issues may arise from liquid which has begun its journey along the intended path for vaporization and arrived at or near the heater, but which is then not vaporized. This may happen if, for example, the wicking action draws liquid towards the heater at a faster rate than it can be vaporized by the heater when activated, or when wicking continues when the heater is not activated. Liquid can then accumulate in the atomizer beyond the amount which can be held in the porous structure and then be released as free liquid into the airflow channel, creating an unwanted escape or leak of liquid.

A potential technique to address unwanted leakage is to minimize any weak points in the structure (by reducing the number of joints between components, for example), or to make any apertures at these weak points as small as possible, or to apply or provide some form of sealing material at or over such weak points. However, it is not desirable to provide a completely sealed reservoir. While such a structure would be watertight and therefore leak-proof, it would also be airtight or close to airtight, restricting air from entering the reservoir. An ingress of air is necessary to equalize the pressure inside the reservoir as the source liquid is consumed, and to allow the continued outward flow of source liquid to the atomizer. Also, it is necessary to maintain the openings through which the liquid leaves the reservoir to reach the atomizer, and capillary action will continue to draw liquid to the atomizer if the heater is activated for vaporization or not.

Accordingly, an alternative approach is proposed to address the leakage problem. Rather than attempting to prevent leaks from the reservoir from occurring, it is proposed to allow/expect some leakage, and arrange for collection of the leaked liquid before it can produce any problems such as spillage or damage to other parts of the electronic cigarette. An element made from absorbent material is disposed within the electronic cigarette to collect and absorb liquid which may escape from the reservoir and find its way along a path or route that does not result in vaporization. Herein, the term "escaped" includes source liquid that has directly leaked from the reservoir or dripped from the wick or heater, and also source liquid has followed the intended path from reservoir to heater for vaporization but which has then condensed back to liquid rather than being delivered as a vapor for inhalation. These mechanisms can all result in source liquid which is free within the electronic cigarette externally from the reservoir and not able to be vaporized, presenting a potential problem if it reaches the electrical power supply. The proposed absorbent element can collect this stray source liquid.

FIG. 4 shows a longitudinal cross-sectional view of a cartomizer component including an absorbent element according to a first example. The cartomizer component 30 houses a reservoir 3 for source liquid and an associated atomizer 40 with a wicking component (which may be a separate wick or a combined wick and heater, for example) that reaches into the interior of the reservoir and which is arranged to generate and deliver vapor into the air flow path 37 for consumption via the mouthpiece 35. Opposite the mouthpiece 35, the cartomizer 30 terminates in a connector 31 configured to make mechanical and electrical connection to a power component housing a battery and circuitry to provide electrical power from the battery to a heating element in the atomizer 40. The connector 31 forms an end wall of the cartomizer 30 which in use abuts a corresponding end wall connector on a power component. In this example, the airflow path 37 extends through this end wall of the cartomizer 30, so the connector 31 has a central aperture 38 forming an air inlet to let air enter the air flow path 37. Other air inlet arrangements are possible, so there may be no air aperture in the end wall.

The reservoir 3 has an annular shape as in the FIGS. 2 and 3 examples, so that its interior storage volume is defined between outer and inner walls 32, 34. Any source liquid that escapes through the outer wall 34 will enter the interior of the cartomizer (defined within an exterior cartomizer housing 39), and may find its way to the connector 31. Any source liquid that escapes through the inner wall 34 will enter the air flow path 37, and may also find its way towards the connector 31. Source liquid may enter the air flow path as a direct leak, or via dripping from a saturated wicking element, as described above.

When the cartomizer 30 is separated from its power component, any liquid in the air flow path 37 can exit through the central aperture 38 of the connector 31. Liquid inside the cartomizer housing 39 may also exit, via any openings or apertures formed where the connector joins the cartomizer housing or where electrical connections extend through the connector (to connect the heater in the atomizer 40 to a battery external to the cartomizer). Thus, source liquid may undesirably escape as spillage from the cartomizer 30. When the cartomizer 30 is connected to a power component 20 by means of the connector 31, this spilled liquid could enter the interior of the power component, and may penetrate to the control circuitry and/or the battery (shown in FIG. 1) and cause the usual problems produced when electrical components are exposed to liquid. The electronic cigarette may thereby be rendered unsafe or inoperable.

To address this, the cartomizer 30 additionally comprises an absorbent element 50, having in this example the form of a flat pad of absorbent material disposed inside the cartomizer housing adjacent to the inner surface of the connector 31. In particular the absorbent element 50 is positioned upstream of the atomizer, having regard to the direction of air flow along the air flow channel 37 through the electronic cigarette when a user inhales on the electronic cigarette. The atomizer 40 lies between the absorbent element 50 and the mouthpiece 35, with respect to the flow direction along the airflow channel 37. The pad 50 has a central aperture aligned with the central aperture 38 in the connector 31, so that it forms part of the side wall of the air flow path 37. Note that the central position of these apertures in this example is merely illustrative; the air flow path may be non-central and/or may comprise more than one air inlet aperture. When positioned in this way, the absorbent material can collect any escaped source liquid in the air flow path 37 before it reaches the air inlet 38, and any escaped source liquid inside the cartomizer housing 39 before it reaches the connector 31. Any collected liquid is absorbed by the absorbent element 50, so that the escape of liquid out of the cartomizer is reduced, inhibited or prevented altogether. As an alternative, the absorbent element may be separated from the air flow path 37 by an intervening wall so that it collects escaped source liquid inside the cartomizer housing only. The absorbent element 50 should be shaped and positioned to accommodate the required electrical connection from the connector 31 to the heater. The electrical connection(s) may pass through or around the absorbent element 50, for example.

Figure 5A:
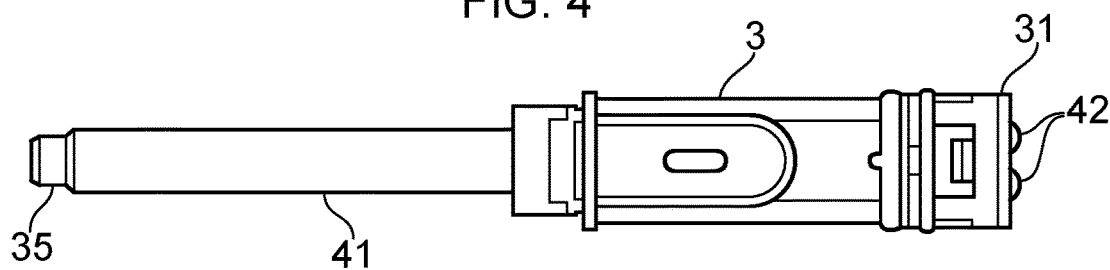
FIG. 5A shows a perspective side view of parts of an example cartomizer.
Figure 5B:
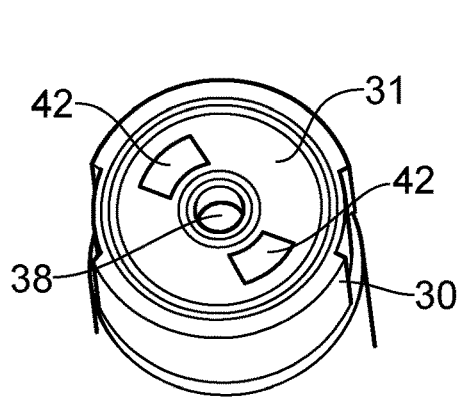
FIG. 5B shows a perspective end view of the cartomizer of FIG. 5A.
Figure 5C:
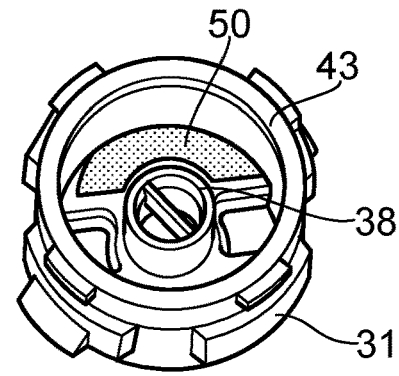
FIG. 5C shows a perspective view of a connector end cap and absorbent element from the cartomizer of FIGS. 5B and 5C.

FIGS. 5A-5C show some perspective views of parts of an example electronic cigarette cartomizer configured in a similar manner to the FIG. 4 example. FIG. 5A shows a wall of a reservoir 3 defining a space forming part of the air flow path and within which lies an atomizer (not shown, and in this example this is a combined wick-and-heater arrangement such as that described with respect to FIG. 3). An air path tube 41 is joined at one end of the reservoir to define the air flow path from the atomizer to the mouthpiece 35. The opposite end of the reservoir is coupled to a connector 31 which in this example can be considered as an end cap forming an end wall of the cartomizer. The end cap 31 is configured for mechanical attachment to a power component (not shown), and includes a pair of electrical contacts 42 to make electrical connection to a battery and control circuit in an attached power component. The parts shown in FIG. 5A would be arranged in an outer cartomizer housing (not shown).

FIG. 5B shows a perspective end view of the end cap connector 31 fitted onto the end of the cartomizer. The circular cross-section of the cartomizer is apparent from this view. The electrical contacts 42 can be seen, arranged diametrically opposite each other, and spaced apart on either side of a central aperture 38 being the air inlet for the cartomizer's air flow path.

FIG. 5C shows a further perspective view of the end cap connector 31, separated from its cartomizer. The connector 31 is positioned so that its internal face, which in use faces into the interior of the cartomizer, is in view. The connector 31 comprises a flat circular wall, which forms the end wall of the cartomizer, and an upstanding peripheral wall 43 around the circular wall. The central aperture 38 can be seen, defined through the circular wall, and the absorbent element 50 (shown as a textured surface) can be seen in the base of the connector 31 against the circular wall. The peripheral wall has a number of protrusions on its outer surface by which the connector 31 engages with the cartomizer housing and/or reservoir walls.

Figure 6A:
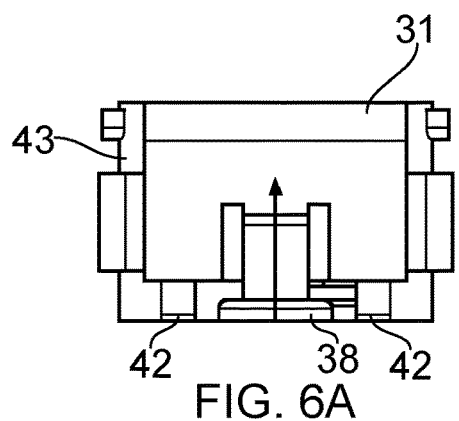
FIG. 6A shows a cross-sectional side view of a further example end cap for a cartomizer.
Figure 6B:
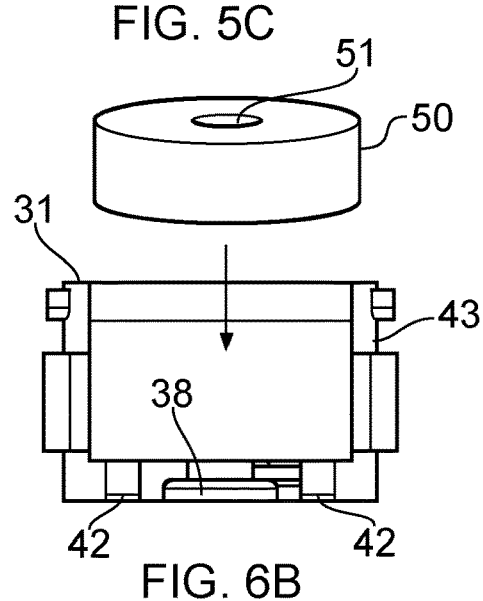
FIG. 6B shows the end cap of FIG. 6A with an example absorbent element.

FIGS. 6A and 6B show cross-sectional views through an example end cap connector. FIG. 6A shows the connector 31, which is similar to the connector of FIGS. 5A-C. The circular end wall has a central aperture 38 as an air inlet for the cartomizer. Two electrical contacts 42 are on the lower surface of the end wall; these may be actual contacts or may be apertures through which contact elements may pass. The annular peripheral wall 43 extends up from the circular wall (in the depicted orientation) to define a recess inside the end cap connector 31.

FIG. 6B shows the end cap connector 31 together with an absorbent element 50 ready for insertion into the recess inside the connector (as indicated by the arrow). The absorbent element has a disc shape, with a width greater than its thickness, and with a central opening 51 which aligns with the air inlet aperture in the end cap when the absorbent element 50 is received in the recess. The width of the absorbent element is substantially the same as the width of the recess so that the absorbent element extends fully across the recess and can capture most if not all incident liquid. The absorbent element 50 may be pushed fully into the recess so that it lies against the inner surface of the end wall, or may be inserted less far so that there is a gap between the absorbent element and the end wall, for example to allow room for expansion of the absorbent element when wet.

The central opening 51 may be smaller than the air inlet aperture or may be absent altogether, if the absorbent element does not present any significant increase in the resistance to draw when a user inhales through the electronic cigarette. For example, it may be made from a material with a sufficiently open structure that air can pass through the absorbent element with little or no impediment to the inhalation air flow rate.

FIGS. 7A-7C show perspective views of another example end cap connector, absorbent element and cartomizer. FIG. 7A shows a perspective view of a connector 31, having a central air inlet aperture 38 in its end wall as before. A pair of further openings 42a (only one properly visible) are formed in the end wall, diametrically opposed about the central aperture 38; these allow electrical contact into the cartomizer.

FIG. 7B shows a perspective view of an absorbent element 50, configured for insertion into the recess in the end cap connector of FIG. 7A. The absorbent element 50 is shaped as a disc, with a diameter around three times its thickness, and a thickness of about 2.5 mm. These are example dimensions only and other sizes and proportions may be selected according to implementation. A central aperture 51 aligns with the central aperture 38 in the connector 31 when the absorbent element 50 is inserted into the recess. Additionally, the absorbent element 50 has a pair of notches 52 cut into its rim; these are arranged diametrically in order to align with the electrical contact openings 42a in the connector 31. The notches 52 may be differently shaped from the approximately square cut-outs shown, and may alternatively comprise holes through the material of the absorbent element 50 in place of notches.

FIG. 7C is a perspective end view of a cartomizer to which the end cap 31 has been fitted, containing the absorbent element (not visible in this view). Electrical contacts 42 are shown, aligned with the openings 42*a*. These may be disposed on a separate end plate which covers the end face of the cartomizer, for example. The central air inlet aperture 38 can be seen. The peripheral side wall 43 of the end cap is held inside the side walls of the cartomizer 30.

Although these examples show the absorbent element positioned inside the cartomizer, against or near the inner surface of an end wall component of the cartomizer such as the connector cap, it may alternatively be located on the outer surface of the cartomizer end wall. For example, it may be stuck to the end wall with adhesive, or a peripheral wall may define a recess to receive and hold the absorbent element, perhaps by a friction fit, or one or more retaining latches or clips or other supports may hold the absorbent element in place so that it is not lost when the cartomizer is separated from its power component. Other positions downstream of the atomizer may also be employed.

The examples thus far have included an absorbent element in the cartomizer component of an electronic cigarette, but an absorbent element may alternatively or additionally be comprised in a power component of an electronic cigarette. Suitably located, it can be arranged to collect and absorb any liquid that enters the power component via its connector (which is likely a vulnerable part of the power component as regards liquid ingress) before the liquid can reach any electronic or electrical parts.

FIG. 8 shows a schematic representation of an example power component comprising an absorbent element. The power component 20 comprises an outer housing 22 which accommodates a battery or cell 5 (which might be recharged via a charging port 52 by which the power component can be connected to an external power supply), and control circuitry. This may comprise any or all of a printed circuit board, a microprocessor, a microcontroller, logic gates, switches, and similar hardware items, plus possibly software, configured for controlling the electronic cigarette. This control includes controlling the supply of electrical power from the battery to the heater in a connected cartomizer, plus other control functions depending on the complexity of the electronic cigarette. These electrical items are at risk of damage and/or malfunction if they come into contact with liquid, so the power component further comprises an absorbent element 50. This is arranged between the end connector 21, by which electrical and mechanical connections are made to a cartomizer, and the electrical items (which may be arranged differently from the depicted configuration, which is purely illustrative). Thus, any source liquid which may have escaped from the reservoir housed in a cartomizer to which the power component is connected, and penetrated the connected connectors 31 (FIGS. 1 and 4) and 21 can be collected by the absorbent element and inhibited or prevented from reaching the battery and/or the control circuitry (control electronics).

FIG. 8 does not depict any air flow path for alignment with a cartomizer air flow path (such as the path 37 in FIG. 4), but the absorbent element 50 and the connector 21 may include suitable apertures for air flow if the primary air inlet for the electronic cigarette is in the power component (as in the FIG. 1 example). Also, appropriate openings (apertures, holes, notches) to enable electrical connections to be made may be present. Also, the absorbent element may be placed on the outer side of the connector 21 rather than adjacent its inner face (for example as discussed above with regard to the cartomizer having an absorbent element on the outer surface of the cartomizer end wall).

The absorbent element may have a porous structure to enable it to absorb incident liquid. It may be formed from a soft, flexible, non-rigid or semi-rigid, and possibly resilient, material. These properties will allow a suitably shaped absorbent element to be conveniently tightly fitted into its intended space so that the space can be fully bridged and liquid may be prevented from readily flowing past the absorbent element. The element may be made from any absorbent material, possibly subject to any restrictions from regulatory requirements governing electronic cigarettes. Possible materials include paper, cardboard, cotton, wool, and other synthetic and natural fabric materials. These materials may all be readily formed into a required shape by cutting or stamping, and are readily available in a range of thicknesses. A further alternative is a sponge material. Natural (animal fiber) sponge or synthetic sponge may be used. Example materials for synthetic sponge include cellulose wood fiber and foamed plastic polymers. Low-density polyether, polyester, PVA (polyvinyl acetate), polyethylene and polypropylene may be used, for example. Sponge absorbent elements may be cut or molded into the required shape and size. Other absorbent materials are not excluded, however. Examples include cellulose acetate filter material, cotton wadding, polyester wadding, absorbent materials used in nappies and sanitary towels, rayon, polyurethane, cellulose sponge, and so-called "post office sponge" (a natural, open cell sponge rubber).

A material of particular interest for the absorbent element is a porous synthetic fibrous material made from polyolefin fibers comprising a mixture of polypropylene and polyethylene. Any proportion of these two materials may be combined as desired, for example 5% polypropylene and 95% polyethylene; 10% polypropylene and 90% polyethylene; 15% polypropylene and 85% polyethylene; 20% polypropylene and 80% polyethylene; 25% polypropylene and 75% polyethylene; 30% polypropylene and 70% polyethylene; 35% polypropylene and 65% polyethylene; 40% polypropylene and 60% polyethylene; 45% polypropylene and 55% polyethylene; 50% polypropylene and 50% polyethylene; 55% polypropylene and 45% polyethylene; 60% polypropylene and 40% polyethylene; 65% polypropylene and 35% polyethylene; 70% polypropylene and 30% polyethylene; 75% polypropylene and 25% polyethylene; 80% polypropylene and 20% polyethylene; 85% polypropylene and 15% polyethylene; 90% polypropylene and 10% polyethylene; or 95% polypropylene and 5% polyethylene; or within ranges close to these values. This fibrous material has a semi-rigid structure that lends itself favorably to formation of the absorbent element by cutting or stamping to the correct size and shape, and also to drilling for the creation of through-holes such as airflow apertures and electrical contact apertures.

Material comprising relatively equal proportions of polypropylene and polyethylene may be used. For example, the material may comprise polypropylene in the range of 40% to 60% and polyethylene in the range of 60% to 40%; or polypropylene in the range of 45% to 55% and polyethylene in the range of 55% to 45%; or polypropylene in the range of 48% to 52% and polyethylene in the range of 52% to 48%; or polypropylene in the range of 49% to 51% and polyethylene in the range of 51% to 49%. Substantially equal proportions of these two materials may be used, so that the material comprises substantially 50% polypropylene and substantially 50% polyethylene. Similar or equal proportions of the polypropylene and polyethylene produce a material which has good hydrophilic properties (it absorbs incident liquid rather than repelling it), and also does not exhibit excessive expansion when it gets wet (i.e. when it has absorbed liquid). Materials formed from less equal proportions of polypropylene and polyethylene are also useful, however. Also, the material may include one or more other materials in addition to polypropylene and polyethylene. These may include the various example absorbent materials discussed above, or may be materials which impart other characteristics to the material, such as a finishing additive comprising nonionic emulsifiers to provide antistatic properties. Such an additive might comprise around 1% of the absorbent material, for example.

The material used for the absorbent element may have an absorbency which is sufficient to retain any leaked liquid until it naturally evaporates from the absorbent material, or may act instead to delay the escape to the external environment of any leaked liquid compared to no absorbent material being present. This will depend at least in part on the rate of any leaks compared to the amount and absorbency properties of the absorbent material used.

An absorbent material which does not expand too much when wet is useful for the absorbent element. This characteristic means that little or no expansion room needs to be provided within the electronic cigarette to accommodate the absorbent element when wetted. Hence, the inclusion of an absorbent element need not significantly increase the size of the electronic cigarette, and/or a larger volume of absorbent material can be included for a given available space. For example, the absorbent element may be made from an absorbent material which expands when wet to increase its volume in the range of 0% to 50%; or 0% to 40%; or 0% to 30%; or 0% to 20%; or 0% to 10%; or 0% to 5% when fully saturated (i.e. when it cannot absorb any more incident liquid). For example, the substantially 50% polypropylene and 50% polyethylene fibrous material discussed above has been found in tests to expand by less than 3% when fully saturated.

The absorbent element may have a flat planar shape, such a round or oval disk or a square or rectangle or other polygon or other regular or irregular shape, depending on the interior cross-section or bore of the part of the electronic cigarette to which it is fitted. As noted, it is useful for the absorbent element to fill the bore where it is installed (i.e. there are no gaps left between the sides of the element and the surrounding wall of the component or other part of the electronic cigarette) so that incident liquid cannot run past the absorbent element and avoid being absorbed. This is not essential however. The absorbent element may have a thickness in the range of 1 mm to 10 mm, for example, although smaller and large thicknesses are not excluded. The thickness chosen will depend on the amount of space available to accommodate the absorbent element, and the absorbency of the material used for the absorbent element; a highly absorbent material may be used with a smaller thickness than a lower absorbency material, for example.

The absorbent material used for the absorbent element may have a density in the range of 0.5 g/cm$^3$ to 10 g/cm$^3$, such as between 0.5 g/cm$^3$ to 2, 3, 4, or 5 g/cm$^3$. For example, a fibrous polypropylene/polyethylene material may have a density of about 0.9 g/cm$^3$. Low density materials minimize the mass added to an electronic cigarette by the inclusion of an absorbent element.

The absorbent element may be incorporated as a permanent feature of the component which houses it, or the component may be configured to allow the absorbent element to be removed by the user. For example, the absorbent element might be held in an end cap of a cartomizer or power component (similar to the cap in FIGS. 5 to 7) which is configured to be removable by the user so that the absorbent element can be extracted. This allows the absorbent element to be temporarily removed for drying if it has become saturated, or allows the absorbent element to be replaced.

The position of the absorbent element is not limited to those depicted and described thus far. It may be installed in any position or location within the electronic cigarette where it can usefully intercept the passage of liquid leaking from the reservoir and/or atomizer and following a path that will not lead to vaporization in an activated atomizer (a leak flow path). This includes paths leading directly away from the atomizer, and paths that deliver liquid to the atomizer where it can then escape as leakage into the airflow path if not vaporized promptly. To this end, the absorbent element is not limited to the shape of a flat pad, such as the planar disc of FIGS. 6 and 7. It can be alternatively be installed in a non-flat shape (either by bending or wrapping of a flat but flexible material, or by use of a curved shape formed by molding, for example). This includes wrapping or overlaying a non-flat surface of a part within the electronic cigarette with a sheet of absorbent material. Also, the absorbent element might be formed with one or more depressions or recesses on a surface facing towards the atomizer (i.e. on the downstream side of the absorbent element) which will act as a dish or cup to aid in collecting liquid and holding it for absorption into the absorbent material. FIG. 9 shows a schematic representation of a cartomizer 30 in which an absorbent element 50 located adjacent the connector 31 has a dished surface 50a facing towards the atomizer 40. In other words, the absorbent element 50 is concave on its downstream face. Other positions for an absorbent element can be chosen as required.

Absorbent elements in accordance with embodiments can be utilized with any configuration of electronic cigarette, not merely those of a generally elongate structure in which a cartomizer and power component connect end to end as in the FIG. 1 example. The electronic cigarette may be generally cylindrical or non-cylindrical, elongate or non-elongate, and components may be arranged linearly (end-to-end) or in parallel (side-by-side); other configurations are also included.

Parts may be variously distributed between components of the electronic cigarette as desired, and the components may be separable from and reconnectable to one another or may be permanently joined or connected together. For example, the atomizer may be in the same component as the reservoir (as in the FIGS. 4 and 9 examples) or may be in a different component; or the control circuitry may be in a different component from the reservoir (as in the FIG. 8 example) or may be in the same component; or the battery may be in a different component from the reservoir (as in the FIG. 8 example) or may be in the same component. The absorbent element may usefully be located anywhere within the electronic cigarette or component of the electronic cigarette where it is able to intercept source liquid which is free from the reservoir and not able to be vaporized, and collect that liquid by absorption. For example, the absorbent element may be situated to protect the battery and/or the control electronics or circuitry (such as a PCB or microcontroller) from exposure to source liquid. An absorbent element placed between the atomizer (and/or the reservoir) and the relevant electrical parts can achieve this; in a separable electronic cigarette it may be incorporated into either the cartomizer component or the power component. In other examples, the absorbent element may be located to collect any escaped liquid that would otherwise be likely to flow out of the component in which the reservoir is housed; this includes a component in a connected state or an unconnected state. Hence, the absorbent element might be positioned to collect liquid in the vicinity of a connection joint for coupling the reservoir component to another component such as a power component, or to collect liquid that might leak from inlets and/or outlets of the air flow path.

An electronic cigarette or component therefor may comprise a single absorbent element, or may comprise two or more absorbent elements to increase the level of protection from leaks. Multiple elements might be located at different places within the electronic cigarette, such as to intercept liquid on different leak flow paths, or might be stacked along the same leak flow path, either in contact or spaced apart. Absorbent elements made from different materials might be included in the same electronic cigarette.

In an alternative, an absorbent element might be positioned downstream of the atomizer where it could collect escaped source liquid in the air flow path to stop the liquid from exiting through the mouthpiece; in which case, the absorbent element may be made from a porous synthetic sponge material made from a mixture of polypropylene and polyethylene in any of the relative proportions described above. FIG. 9 indicates a possible position for such an absorbent element 60, shown in phantom. To this end, a component of an electronic vapor provision device, where the device has a reservoir for storing source liquid, an atomizer for vaporizing source liquid from the reservoir and delivering vapor into an air flow path through the device, and an electrical power supply for providing electrical power to the atomizer, may comprise an absorbent element located to collect source liquid escaped from the reservoir, the absorbent element made from an absorbent material made from a mixture of polypropylene and polyethylene. The absorbent element may be upstream or downstream of the atomizer with respect to the air flow direction along the air flow path.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in future.

The invention claimed is:

1. A component of an electronic vapor provision device, the electronic vapor provision device having a reservoir for storing source liquid, an atomizer for vaporizing source liquid from the reservoir and delivering vapor into an air flow path through the electronic vapor provision device, and an electrical power supply for providing electrical power to the atomizer, the component comprising:

an absorbent element positioned so as to collect free source liquid escaped from the reservoir without being vaporized and to inhibit the free source liquid from exiting the component and from reaching the electrical power supply, the absorbent element located so as to be downstream of the atomizer with respect to an air flow direction along the air flow path when the component is assembled into the electronic vapor provision device, the absorbent element comprising cellulose.

2. The component according to claim 1, wherein the absorbent element is located so as to be between the atomizer and the electrical power supply in the assembled electronic vapor provision device along a liquid flow path from the atomizer to the electrical power supply.

3. The component according to claim 1, wherein the electrical power supply comprises a battery.

4. The component according to claim 1, wherein the electrical power supply comprises control circuitry for controlling the provision of electrical power to the atomizer.

5. The component according to claim 1, wherein the absorbent element is located adjacent to an end face of the component.

6. The component according to claim 5, wherein the end face of the component is at an end of the component connectable to another component of the electronic vapor provision device.

7. The component according to claim 1, wherein the component is a cartomizer component housing the reservoir and the atomizer and is connectable to a power component housing the electrical power supply, and the absorbent element is located so as to inhibit the escaped liquid from leaving the cartomizer component, and also from reaching the electrical power supply when the cartomizer component is connected to the power component.

8. The component according to claim 7, wherein the absorbent element is mounted within an end cap of the cartomizer component which is configured to allow electrical contact with an electrical power supply housed in a power component of the electronic vapor provision device to which the component is connectable.

9. The component according to claim 1, wherein the component is a power component housing the electrical power supply and connectable to a cartomizer component housing the reservoir and atomizer, and the absorbent element is located so as to inhibit the escaped liquid from reaching the electrical power supply when the power component is connected to the cartomizer component.

10. The component according to claim 1, wherein the absorbent element has a planar shape and a thickness orthogonal to a plane of the planar shape in the range of 1 mm to 10 mm.

11. The component according to claim 1, wherein a volume of the absorbent element increases by not more than 20% when fully saturated.

12. The component according to claim 1, wherein a volume of the absorbent element increases by not more than 10% when fully saturated.

13. The component according to claim 1, wherein a volume of the absorbent element increases by not more than 5% when fully saturated.

14. The component according to claim 1, wherein a volume of the absorbent element increases by not more than 3% when fully saturated.

15. The component according to claim 1, wherein a volume of the absorbent element increases by not more than 1% when fully saturated.

16. An electronic vapor provision device comprising the component according to claim 1.

17. The electronic vapor provision device according to claim 16, in which the component is separably connectable to another component of the electronic vapor provision device.

18. The electronic vapor provision device according to claim 16, wherein the component is a permanent component of the electronic vapor provision device.

\* \* \* \* \*